United States Patent
Hölderich et al.

(10) Patent No.: US 8,921,605 B2
(45) Date of Patent: Dec. 30, 2014

(54) PROCESS FOR PREPARING PSEUDOIONONE

(75) Inventors: Wolfgang Hölderich, Frankenthal (DE); Verena Ritzerfeld, Aachen (DE); Bernhard Markus Ernst Russbüldt, Düren (DE); Erhard Henning Fleischhauer, Aachen (DE); Werner Bonrath, Basel (CH); Reinhard Karge, Basel (CH); Jan Schütz, Basel (CH)

(73) Assignee: DSM IP Assets B.V., Heerlen (NL)

( * ) Notice: Subject to any disclaimer, the term of this patent is extended or adjusted under 35 U.S.C. 154(b) by 45 days.

(21) Appl. No.: 13/810,985

(22) PCT Filed: Jul. 19, 2011

(86) PCT No.: PCT/EP2011/062299
§ 371 (c)(1),
(2), (4) Date: Aug. 5, 2013

(87) PCT Pub. No.: WO2012/022562
PCT Pub. Date: Feb. 23, 2012

(65) Prior Publication Data
US 2013/0310607 A1    Nov. 21, 2013

(30) Foreign Application Priority Data
Jul. 21, 2010  (EP) .................................. 10170332

(51) Int. Cl.
| | | |
|---|---|---|
| *C07C 45/74* | (2006.01) | |
| *C07C 45/00* | (2006.01) | |
| *B01J 23/92* | (2006.01) | |
| *B01J 23/10* | (2006.01) | |
| *B01J 37/08* | (2006.01) | |

(52) U.S. Cl.
CPC ................. *B01J 23/10* (2013.01); *C07C 45/00* (2013.01); *C07C 45/74* (2013.01); *B01J 23/92* (2013.01); *B01J 37/086* (2013.01)
USPC ........................................................ 568/390

(58) Field of Classification Search
USPC ........................................................ 568/390
See application file for complete search history.

(56) References Cited

U.S. PATENT DOCUMENTS 7,098,366 B2 *   8/2006   Sigl et al. ...................... 568/390

FOREIGN PATENT DOCUMENTS

WO     WO 03/047748     6/2003

OTHER PUBLICATIONS

International Search Report for PCT/EP2011/062299, mailed Nov. 24, 2011.
Russbueldt, B.M. et al., "New Rare Earth Oxide Catalysts for the Transesterification of Triglycerides with Methanol Resulting in Biodiesel and Pure Glycerol", Journal of Catalysis, vol. 271, No. 2, (May 4, 2010), pp. 290-304.

* cited by examiner

*Primary Examiner* — Sikarl Witherspoon
(74) *Attorney, Agent, or Firm* — Nixon & Vanderhye P.C.

(57) ABSTRACT

Use of pure lanthanum oxide which is obtained by calcination of oxygen-containing lanthanum salts at temperatures of at least 700° C. as heterogeneous catalyst in the aldol condensation of citral and acetone to give pseudoionone, and process for the preparation of pseudoionone by aldol condensation of citral and acetone in the liquid phase using pure lanthanum oxide.

1 Claim, 4 Drawing Sheets

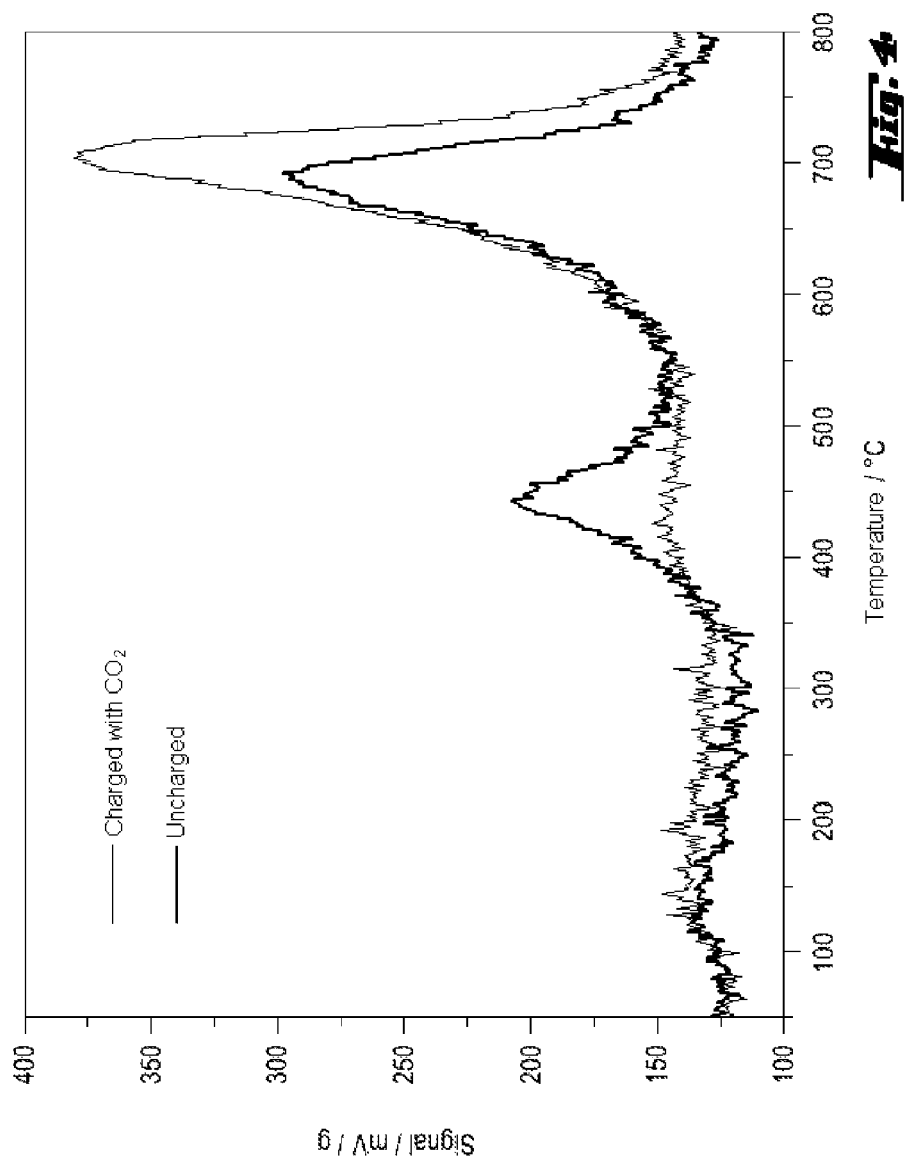

PROCESS FOR PREPARING PSEUDOIONONE

This application is the U.S. national phase of International Application No. PCT/EP2011/062299, filed 19 Jul. 2011, which designated the U.S. and claims priority to EP Application No. 10170332.0, filed 21 Jul. 2010, the entire contents of each of which are hereby incorporated by reference.

The present invention relates to a process for the preparation of pseudoionone and the catalysts used therein. More specifically, the present invention relates to the preparation of pseudoionone from citral (E/Z-3,7-dimethyl-2,6-octadien-1-al) and acetone in liquid phase with a heterogeneous catalyst, where the catalyst is lanthanum oxide that has been treated and/or prepared in a particular way. The invention also relates to the lanthanum oxide catalyst produced in this way.

Pseudoionone (6,10-dimethyl-3,5,9-undecatrien-2-one) has juvenile hormone activity and is an important intermediate in the manufacture of vitamin A and E, carotenoids and fragrances. It is obtained primarily by the base-catalyzed aldol reaction of citral with acetone and the elimination of water, i.e. aldol condensation. The use of heterogeneous catalysts, particularly on inert supports, is advantageous since they can be easily separated off from the reaction medium and, optionally after regeneration, can be reused several times.

WO 2003/047747 and WO 2003/047748 (publ. Jun. 12, 2003) describe metal oxide catalysts based on γ-aluminum oxide, their use during the aldol condensation of citral and acetone to give pseudoionone, and also special columns for carrying out the reaction by reactive distillation. The metal oxides are oxides of the elements with the atomic numbers 39 (Y) and 57 (La)-71 (Lu), with yttrium oxide and praseodymium oxide being emphasized as being preferred. When using a catalyst of 5% Pr on γ-$Al_2O_3$, in the 24 hour operation, pseudoionone was obtained with a yield of 66.7% and a selectivity of 97.3% based on citral. The concentration of the active components based on the total weight of the supported catalyst is in the range of 5 to 12% by weight, preferably 7.5 to 10% by weight. Whereas, as a result of extensive screening investigations, γ-$Al_2O_3$ has proven to be a particularly suitable support material, which relates to the activity of the catalyst, it is emphasized that both the geometry of the catalyst support and also the maintenance of the aforementioned concentrations are of decisive importance for obtaining good space-time yields.

To produce the supported Pr catalyst, the support was impregnated with a praseodymium nitrate stock solution of 1170 g of praseodymium oxide, 2276 g of 65% aqueous nitric acid and 1557 g of water, which was diluted, according to the liquid absorption of the support, with completely deionized (demineralized) water. Drying was carried out in the drying cabinet at 120° C. and then calcination for 2 hours at 450° C.

DE 102 38 40 A1 (publ. Feb. 26, 2004) describes a process and an apparatus for the continuous preparation of relatively long-chain carbonyl compounds using the example of preparing pseudoionone from citral and acetone using a heterogeneous catalyst of 5% Pr on γ-$Al_2O_3$ (prepared by impregnation of γ-$Al_2O_3$ with an aqueous solution of Pr nitrate and excluding calcination). A yield of 82.6% and a selectivity of 97.2% based on citral is achieved. Preferred catalysts are given as, on the one hand, compounds comprising elements of the lanthanum oxide series, in particular La, Ce and/or Pr, in a concentration of 0.1-20% by weight, preferably 1-10% by weight, on aluminum oxide.

In order to avoid the aforementioned disadvantages, i.e. the precise maintenance of the ratios during the production of the supported catalysts, and moreover the formation of oxide mixed phases during the calcination, which reduce the catalyst activity, particularly when used at relatively high temperatures, the object consisted in developing non-supported heterogeneous catalysts from the lanthanum oxide series which produce good yields and high selectivities during the aldol condensation of citral and acetone to give pseudoionone.

This object was achieved by finding unsupported lanthanum oxide catalysts which catalyze the aldol condensation of citral and acetone to give pseudoionone in high yield and selectivity if they are produced in a certain way.

In J. Catal. 271, 290-304 (2010), B. Russbueldt et al. describe pure rare earth oxides which are suitable as catalysts for the transesterification of triglycerides with methanol. Using the example of $La_2O_3$, the production of a pure lanthanoid oxide catalyst is described. $La_2O_3$ is dissolved in 65% aqueous nitric acid and the solution is diluted with water. By adding an aqueous solution of oxalic acid dihydrate, lanthanum oxalate is precipitated out; after filtration and washing several times with water, this is dried at 120° C. Heating (calcination) to 900° C. in a muffle furnace for 12 hours and cooling in a desiccator gives pure $La_2O_3$ as a white powder, which was characterized by X-ray diffraction (XRD). An improvement in catalyst properties could be achieved by reducing the calcination temperatures to 700° C., as a result of which sintering effects were minimized.

It has been found that pure lanthanum oxides produced in this way are also very highly suitable as heterogeneous catalysts for the aldol condensation of citral and acetone to give pseudoionone.

The present invention therefore relates to the use of pure lanthanum oxides which are obtained by calcining oxygen-containing lanthanum salts at temperatures of at least 700° C. as heterogeneous catalysts during the preparation of pseudoionone from citral and acetone, and to a process for the preparation of pseudoionone from citral and acetone in the liquid phase in the presence of these lanthanum oxide catalysts.

The aldol condensation of citral with acetone to give pseudoionone takes place in the liquid phase in a manner known per se, but in the presence of pure, support-free lanthanum oxide as heterogeneous catalyst. Since citral is present as isomer mixture, the pseudoionone is also present as a mixture of (3E,5Z)- and (3E,5E)-6,10-dimethylundeca-3,5,9-trien-2-one, from which the individual components can be isolated if desired.

The reaction is expediently carried out in a temperature range of 140 to 250° C., preferably in a range of 160 to 200° C. and under atmospheric pressure or pressures of 1 to 6 bara. At lower temperatures, the yield is so low that the process is no longer of interest for commercial application. An excess of acetone is used in the process, the best yields being achieved using in the range 10-2:1 mol/mol. As the examples demonstrate, the process is intended for discontinuous operation, although a configuration for continuous operation is in principle no problem for the person skilled in the art.

The ratio of catalyst:citral is expediently in the range of 1:1000 to 1:10, preferably in the range of 1:100 to 1:20 (mol/mol).

The catalyst can be used several times, although its activity decreases (water absorption). It should therefore be regenerated, i.e. re-calcined at 700 to 900° C., at regular intervals, which can be easily determined empirically.

Suitable starting compounds for the preparation of the pure lanthanum oxide, $La_2O_3$, are oxygen-containing lanthanum salts or lanthanum salts which can per se be converted into such, for example lanthanum oxide, lanthanum nitrate, lanthanum carbonate and lanthanum oxalate and which lose all water and $CO_2$ as a result of calcination at 700 to 900° C. Storage under an inert gas and in the presence of water-binding chemicals, such as e.g. in a desiccator, is therefore expedient.

It is also possible to use pure, unsupported oxides of other lanthanoid elements, e.g. of Nd or Pr, in the present aldol condensation as catalysts, but with poorer yields and/or lower selectivity.

The following examples illustrate the present invention in detail.

Chemicals Used

Citral was acquired with a purity of 95% as an isomer mixture of cis (geraniol) and trans (neral) from Acros, untreated lanthanum oxide from Fluka with a purity of 99.98%. Technical-grade acetone was used which can contain up to 1% water. Experiments showed that, compared with the water which is formed during the reaction, this has no influence on the experimental results.

Synthesis of Lanthanum Oxide 50 g (0.15 mol) of untreated lanthanum oxide (Fluka) were converted to the nitrates by adding 68.39 ml of concentrated nitric acid and 1.5 l of demineralized water. During this, the solution was stirred and gently heated in order to speed up the dissolution process. After cooling the solution to room temperature, 84.27 g (0.67 mol, 1.5 equiv.) of oxalic acid, dissolved in 500 ml of demineralized water, were added with stirring and lanthanum oxalate was precipitated out. Decantation and filtration through a Buchner funnel were then carried out. The resulting white solid was dried overnight in a drying cabinet at 110° C. 78.43 g (0.145 mol, 94.3% of theory) of lanthanum oxalate were obtained. 2 g of the lanthanum oxalate were then calcined in air in a tubular furnace at 650° C. for 18 hours. After cooling to 50° C. in the stream of nitrogen, the prepared, white lanthanum oxide was transferred to a Schlenk tube filled with argon. A further 6 g of lanthanum oxalate were calcined to lanthanum oxide for 18 hours in the muffle furnace at 700° C., cooled in the desiccator and likewise stored in a Schlenk tube under argon.

Experimental Procedure During the Aldol Condensation

All of the experiments were carried out batchwise in autoclaves with a capacity of 75 ml. These were provided with a pressure gauge and a valve. The experiments were carried out on a combined heating/stirring plate which was provided with a heating muff for the purposes of distributing the heat uniformly on the autoclaves. A Eurotherm controller with thermocouple was used to establish the particular experiment temperature. Prior to the experimental series, the autoclaves were checked for tightness. For this purpose, the autoclaves were filled with compressed air and placed in a water bath.

An acetone:citral mixture was prepared (molar ratio 12:1). Then, 1 g of the particular catalyst was weighed into a glass inlet provided with a stirrer fish and topped up with 30 ml of the respective citral:acetone solution. Here, the empty weight and also the weight of the filled glass inlet was determined. The filled glass inlet was then placed in the autoclave and the latter was screwed tight. The autoclave was provided with the heating muff and the thermocouple and the experiment temperature was established using the Eurotherm controller. The experiment time was 3 hours for all of the experiments. The time measurement started upon reaching the experiment temperature. When the experiment was complete, the autoclave was cooled in an ice bath and opened. The gas inlet was weighed again and the reaction mixture was centrifuged. A GC sample with dodecane as standard was yielded from the now clear reaction solution. The catalyst was freed from citral remains, dried and characterized with the help of X-ray analysis. Some catalysts were used a second time in order to test their activity.

Apparatuses and Methods Used

Gas Chromatography (GC)

Analysis of the reaction mixture was carried out using an FS-FFAP column (25 m; CS25178-5) in an HP 6890 Plus gas chromatograph.

X-Ray Measurement (XRD)

The X-ray spectra were measured using a powder diffractometer from Siemens D 5000. The anode used consisted of copper.

Surface Determination in Accordance with Brunauer, Emmett and Teller (BET)

The samples were investigated using a Micrometics ASAP 2000. Firstly, the samples were baked-out and helium was used to ascertain the dead volume. The adsorption and desorption isotherms were then recorded with nitrogen.

Thermogravimetry (TG)

The samples were measured with the help of a Netzsch STA 409C with $Al_2O_3$ as reference. The analysis was started at RT and ran to 1110° C., at a heating rate of 2.0 K/min.

It is clear from the thermogravimetry that a calcination above 700° C. is the most sensible if a pure lanthanum oxide phase is to be obtained.

Temperature-Programmed Desorption (TPD)

The measurement was carried out with $CO_2$ as probe molecule with the TPD 1100 apparatus from Thermodefinition. For this purpose, the samples were baked-out at 300° C. in a stream of nitrogen and then charged with $CO_2$ at 100° C. for 1 hour in order to avoid physisorption as far as possible. Heating was then carried out to 150 to 200° C. and inert gas was used to remove physisorbed $CO_2$. Afterwards, the temperature program was started and the desorption of $CO_2$ was recorded with time. In the case of a second sample, the TPD curve was recorded without charging.

DESCRIPTION OF THE FIGURES

Adsorption/desorption isotherms for $N_2$ of lanthanum oxide 900° C., catalyst C BET surface area: 5.99 m$^2$/g Micropore area and volume: 0 cm$^3$/g

FIG. 4: TPD investigation of lanthanum oxide 900° C., catalyst C

Figure 1:
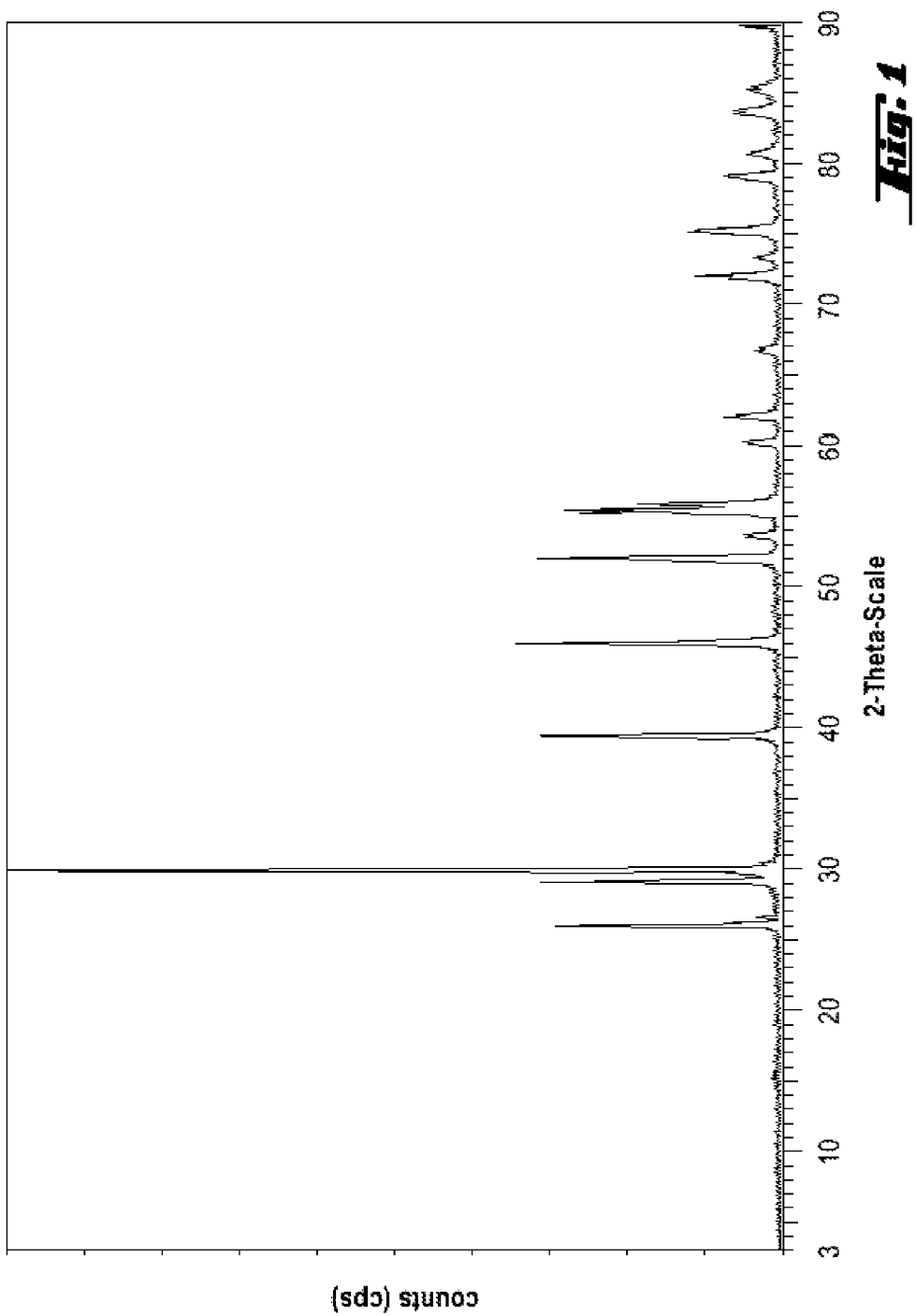
FIG. 1: X-ray spectrum of lanthanum oxide 900° C., catalyst C.
Figure 2:
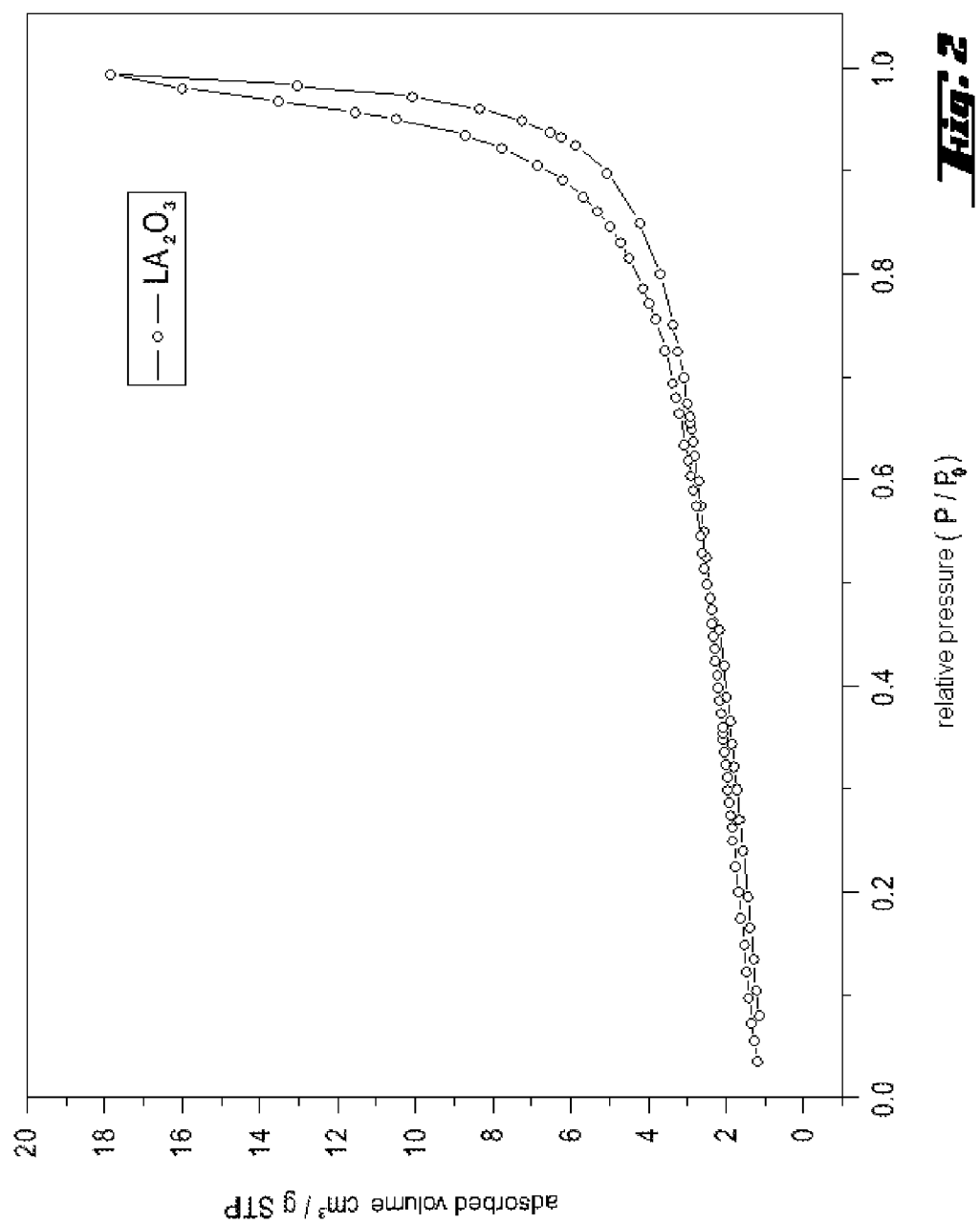
FIG. 2: BET measurement of lanthanum oxide 900° C., catalyst C.
Figure 3:
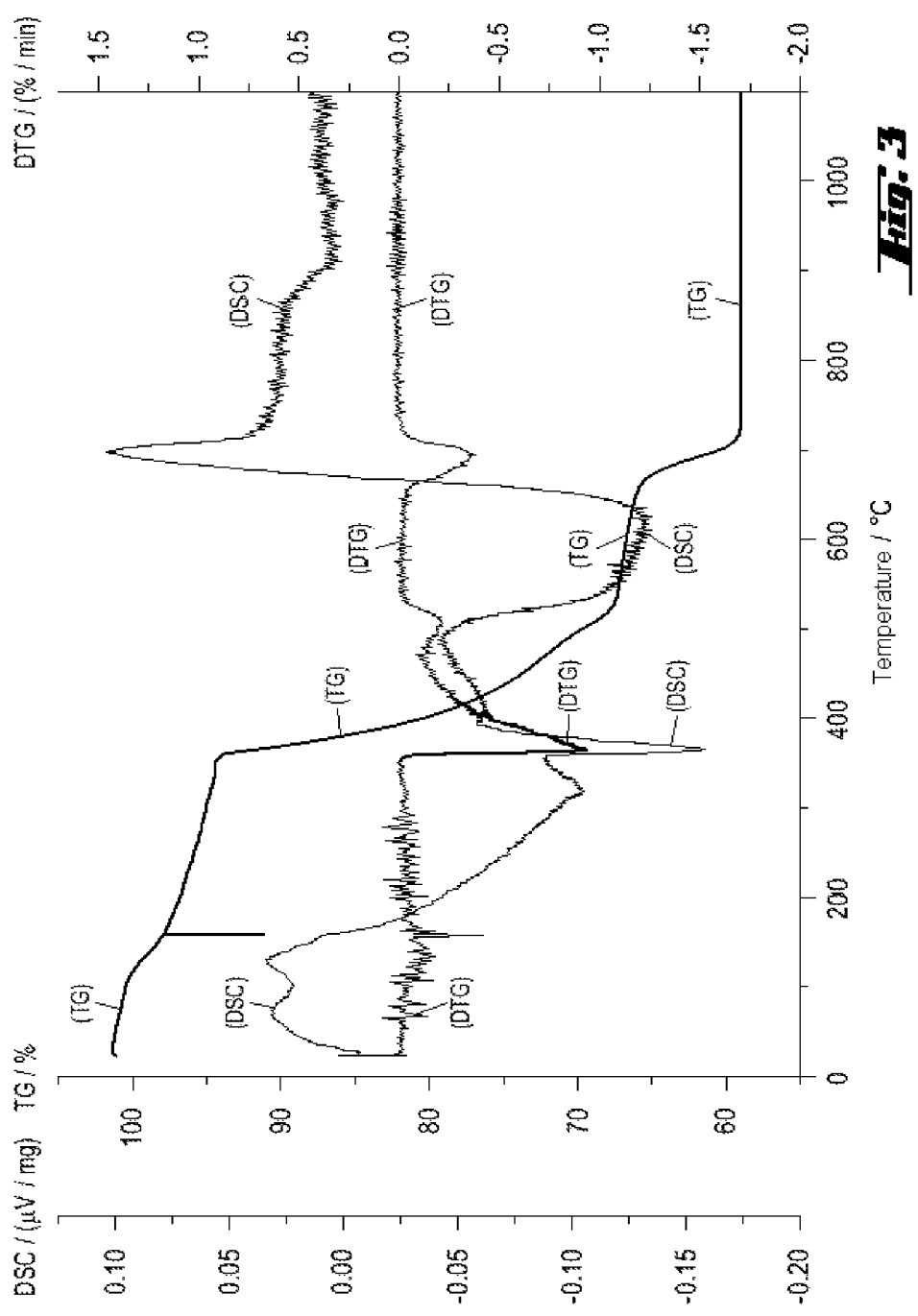
FIG. 3: Thermogravimetric analysis of lanthanum oxalate.

The thin black curve was recorded after baking out the sample to 300° C. and subsequent charging with $CO_2$ and the bold black curve was recorded without charging. As can be seen, both curves exhibit a strong desorption band at 700° C. Moreover, in the case of the red curve, a further desorption peak at 450° C. is evident. On the one hand, this can mean that the centers are very strongly basic and therefore only release the probe molecule again at very high temperatures. On the other hand, it is also possible that no adsorption of the $CO_2$, but a reaction to give a stable carbonate phase has proceeded, as a result of which $CO_2$ can likewise only desorb again with difficulty: the formation of carbonate phases, however, appears more likely since the desorption peaks at 450° C. and 700° C. are in agreement with the decomposition of the carbonates $La_2(CO_3)O_2$ and $La_2(CO_3)_2O$ and the weight loss associated therewith in the TG.

The following examples demonstrate the catalytic effectiveness of unsupported catalysts of pure lanthanum oxide for the aldol reaction of citral and acetone to give pseudoionone.

EXAMPLE 1

16.29 g of $La_2O_2$ were dissolved in 22.9 ml of $HNO_3$ 65% and diluted to 500 ml with water. A solution of 20.80 g of oxalic acid.2 $H_2O$ in 500 ml of water was added thereto. The precipitated lanthanum oxalate $La_2(C_2O_4)_3$ was filtered off, washed with distilled water and dried for 16 hours at 120° C. Finally, the $La_2(C_2O_4)_2$ was heat-treated at three different temperatures, namely 650° C. (Cat A), 700° C. (Cat B) and 900° C. (Cat C), room temperature–target temperature/12 hours and at target temperature ° C./12 hours isothermally to give pure $La_2O_3$ and cooled in a desiccator over KOH. Lanthanum oxide D untreated means the uncalcined product commercially available from Fluka.

For the catalysis experiments, 23.19 g of acetone, 5.01 g of citral, molar ratio (acetone:citral) 12:1, and 1 g of the pure $La_2O_3$ were used. The reaction is carried out in a 75 ml autoclave with glass insert for 3 hours at 200° C. and an autogenous pressure of 25 bar.

TABLE 1

Catalytic effectiveness of pure lanthanum oxide in the aldol reaction of citral and acetone.

| | Catalyst | | | |
|---|---|---|---|---|
| | $La_2O_3$ A 650° C. | $La_2O_3$ B 700° C. | $La_2O_3$ C 900° C. | $La_2O_3$ D untreated |
| Conversion | 76.9% | 78.8% | 93.4% | 76.2% |
| Selectivity | 78.9% | 76.6% | 84.3% | 78.7% |
| Yield | 60.7% | 60.4% | 78.7% | 59.9% |

X-ray analysis revealed that a calcination above 700° C. is necessary in order to obtain the pure oxide phase.

EXAMPLE 2

This example demonstrates the catalytic effectiveness of unsupported catalysts of pure neodymium oxide or praseodymium oxide for the aldol reaction.

The catalysts were prepared in the same way as described in example 1. However, the calcination temperatures were only 650 (Cat E and H) or 700° C. (Cat F and I) since such a temperature suffices to produce the pure oxide phases. For the catalysis experiments, 23.19 g of acetone, 5.01 g of citral and 0.4 g of the pure oxide were used. The reaction was carried out in a 75 ml autoclave with glass insert for 3 hours at 200° C.

Also for the catalysis experiments listed in example 2, 23.19 g of acetone, 5.01 g of citral, molar ratio (acetone:citral) 12:1, and 1 g of the catalyst used in each case were used. The reaction was carried out in a 75 ml autoclave with glass insert for 3 hours at 200° C. and an autogenous pressure of 25 bar.

TABLE 2

Catalytic effectiveness of pure neodymium oxide and praseodymium oxide in the aldol reaction of citral and acetone.

| | Catalyst | | | | | |
|---|---|---|---|---|---|---|
| | $Nd_2O_3$ E 650° C. | $Nd_2O_3$ F 700° C. | $Nd_2O_3$ G untreated | $Pr_6O_{11}$ H 650° C. | $Pr_6O_{11}$ I 700° C. | $Pr_6O_{11}$ J untreated |
| Conversion | 14.1% | 60.6% | 53.2% | 6.9% | 54.7% | 66.8% |
| Selectivity | 64.1% | 79.3% | 80.3% | 54.2% | 77.2% | 79.2% |
| Yield | 9.0% | 48.1% | 42.8% | 3.7% | 42.2% | 53.0% |

EXAMPLE 3

This example shows the influence of the temperature on conversion, selectivity and yield of the aldol reaction. Here, all experiments were carried out with 1 g of $La_2O_3$ 900° C., catalyst C, a molar ratio of 12:1 (acetone:citral) at 200° C. and 3 hour reaction time.

TABLE 3

Influence of the temperature on the catalytic activity.

| Temperature ° C. | Conversion | Selectivity | Yield |
|---|---|---|---|
| 60 | 0.6% | 0.0% | 0.0% |
| 80 | 0.1% | 0.0% | 0.0% |
| 120 | 17.4% | 51.7% | 9.0% |
| 160 | 69.9% | 87.5% | 78.7% |
| 200 | 93.4% | 84.3% | 78.7% |

A sharp temperature line at 160° C. was found, at which the reaction gets going to an increased extent.

EXAMPLE 4

This example shows the influence of the amount of catalyst on the catalytic activity. Here, all experiments were carried out with $La_2O_3$ 900° C. catalyst C, a molar ratio of 12:1 (acetone:citral) at 200° C., an autogenous pressure of 25 bar and 3 hour reaction time.

TABLE 4

Influence of the amount of catalyst on the catalytic activity.

| Amount of catalyst [g] | Conversion | Selectivity | Yield |
|---|---|---|---|
| 0.4 | 53.2% | 74.3% | 39.6% |
| 0.6 | 65.9% | 72.0% | 47.4% |
| 0.8 | 75.5% | 67.1% | 50.7% |
| 1 | 81.4% | 64.1% | 52.2% |
| 2 | 84.9% | 54.2% | 46.0% |

As expected, the conversion increases with increasing amount of catalyst. However, the selectivity drops.

EXAMPLE 5

This example shows the recyclization of the catalyst without regeneration. Here, all experiments were carried out with 1 g of $La_2O_3$ 900° C. catalyst C, a molar ratio of 12:1 (acetone:citral) at 200° C., an autogenous pressure of 25 bar and 3 hour reaction time.

TABLE 5

Recyclization of the catalyst without regeneration.

| Feed | Conversion | Selectivity | Yield |
|---|---|---|---|
| 1 | 86.8% | 70.2% | 60.9% |
| 2 | 87.9% | 75.2% | 66.0% |
| 3 | 79.2% | 77.4% | 61.2% |
| 4 | 49.6% | 77.5% | 38.43% |
| 5 | 49.0% | 75.4% | 37.0% |
| 6 | 45.5% | 74.5% | 33.9% |

EXAMPLE 6

This example shows the recyclization of the catalyst with 15-hour regeneration at 300° C. Here, all experiments were carried out with 1 g of $La_2O_3$ 900° C. catalyst C, a molar ratio of 12:1 (acetone:citral) at 200° C., an autogenous pressure of 25 bar and 3 hour reaction time.

TABLE 6

Recyclization of the catalyst with 15 h regeneration at 300° C.

| Feed | Conversion | Selectivity | Yield |
|---|---|---|---|
| 1 | 75.8% | 71.4% | 54.1% |
| 2 | 48.9% | 78.0% | 38.2% |
| 3 | 54.1% | 79.3% | 42.9% |
| 4 | 31.0% | 74.2% | 23.0% |
| 5 | 22.6% | 69.5% | 15.7% |
| 6 | 27.5% | 75.3% | 20.7% |

EXAMPLE 7

This example shows the recyclization of the catalyst with 15-hour regeneration at 900° C. Here, all experiments were carried out with 1 g of $La_2O_3$ 900° C. catalyst C, a molar ratio of 12:1 (acetone:citral) at 200° C., an autogenous pressure of 25 bar and 3 hour reaction time.

TABLE 7

Recyclization of the catalyst with 15 h regeneration at 900° C.

| Feed | Conversion | Selectivity | Yield |
|---|---|---|---|
| 1 | 88.7% | 66.6% | 59.1% |
| 2 | 91.2% | 59.7% | 54.4% |
| 3 | 91.2% | 66.6% | 60.8% |
| 4 | 91.2% | 59.3% | 54.0% |
| 5 | 90.7% | 54.8% | 49.6% |
| 6 | 92.1% | 44.2% | 40.7% |

It is evident from the recyclization experiments that a regeneration of the catalyst between the feeds is expedient. The regeneration temperature selected here should be very high since in the course of the reaction different lanthanum phases can be formed, the formation of which can be reversed by the regeneration.

EXAMPLE 8

This example shows the influence of the mixing ratio acetone:citral on the catalytic activity. Here, all experiments were carried out with 1 g of $La_2O_3$ 900° C. catalyst C at 200° C., an autogenous pressure of 25 bar and 3 hour reaction time.

TABLE 8

Influence of the mixing ratio on the catalytic activity.

| Molar mixing ratio Acetone:citral | Conversion | Selectivity | Yield |
|---|---|---|---|
| 12:1 | 66.9% | 70.9% | 47.4% |
| 10:1 | 77.2% | 68.7% | 53.0% |
| 8:1 | 71.2% | 72.5% | 51.6% |
| 6:1 | 76.8% | 71.3% | 54.8% |
| 4:1 | 83.5% | 71.3% | 59.6% |
| 2:1 | 85.1% | 64.0% | 54.5% |
| 1:1 | 84.3% | 41.1% | 34.6% |

It was found that a reduction in the acetone:citral ratio has a positive influence on the yield. However, as soon as the ratio becomes too low, i.e. drops below 2:1, yield and selectivity drop sharply since, during the reaction, the result is the formation of a two-phase system and diffusion problems arise.

The invention claimed is:
1. A process for the preparation of pseudoionone which comprises conducting a liquid phase aldol condensation of citral and acetone in the presence of a heterogeneous catalyst consisting of pure lanthanum oxide which is a calcined product of oxygen-containing lanthanum salts at temperatures of at least 700° C.

* * * * *